United States Patent [19]
Zadini et al.

[11] Patent Number: 5,411,486
[45] Date of Patent: May 2, 1995

[54] NEEDLE STICK PROTECTOR FOR AUTOMATIC CANNULATION DEVICES

[76] Inventors: Filiberto Zadini, 16814 Rayen St., North Hills, Calif. 91343; Giorgio Zadini, 2237 Hilltop La., Camarillo, Calif. 93012

[21] Appl. No.: 95,653

[22] Filed: Jul. 21, 1993

[51] Int. Cl.⁶ .............................................. A61M 5/00
[52] U.S. Cl. .................................. 604/198; 604/165; 128/919
[58] Field of Search ............... 604/198, 195, 192, 187, 604/263, 264, 218, 165, 170, 164; 128/760, 763, 919

[56] References Cited
U.S. PATENT DOCUMENTS

| | | | |
|---|---|---|---|
| 5,312,361 | 5/1994 | Zadini et al. | 604/165 |
| 5,312,372 | 5/1994 | Deharde et al. | 604/198 |
| 5,328,482 | 7/1994 | Sircom et al. | 604/164 |
| 5,336,187 | 8/1994 | Terry et al. | 604/198 X |

*Primary Examiner*—John D. Yasko

[57] ABSTRACT

A needle stick protector for Automatic Cannulation Devices wherein a needle guard is automatically advanced over the needle of the Automatic Cannulation device to enclose the needle tip, such an advancement occurring automatically, being self initiated and self sustained upon blood vessel penetration by said needle. The needle guard or protective sleeve accomplishes the dual function of propelling a catheter into a blood vessel and of shielding the needle tip of the Automatic Cannulation Device by fully enclosing it.

11 Claims, 18 Drawing Sheets

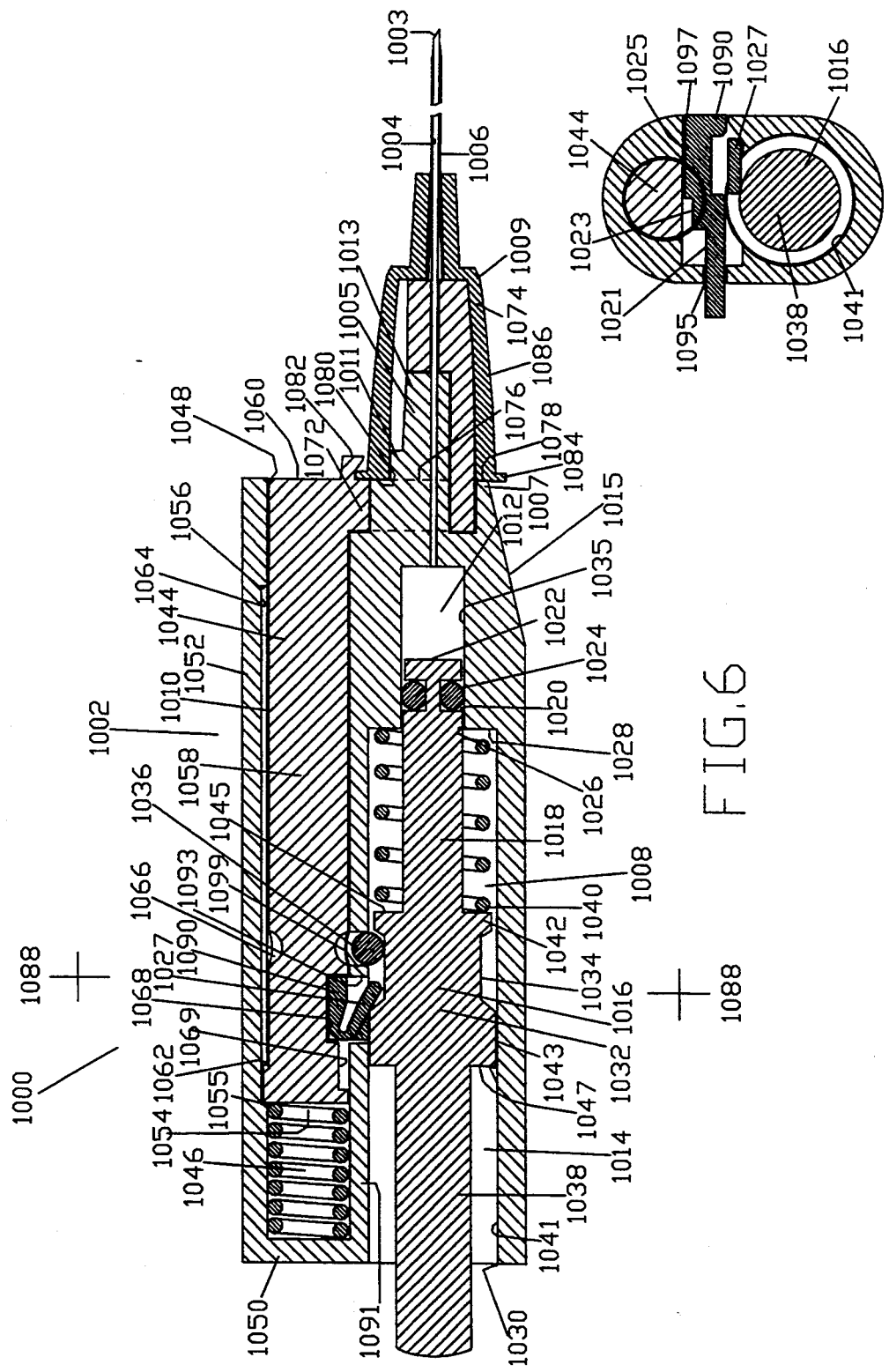

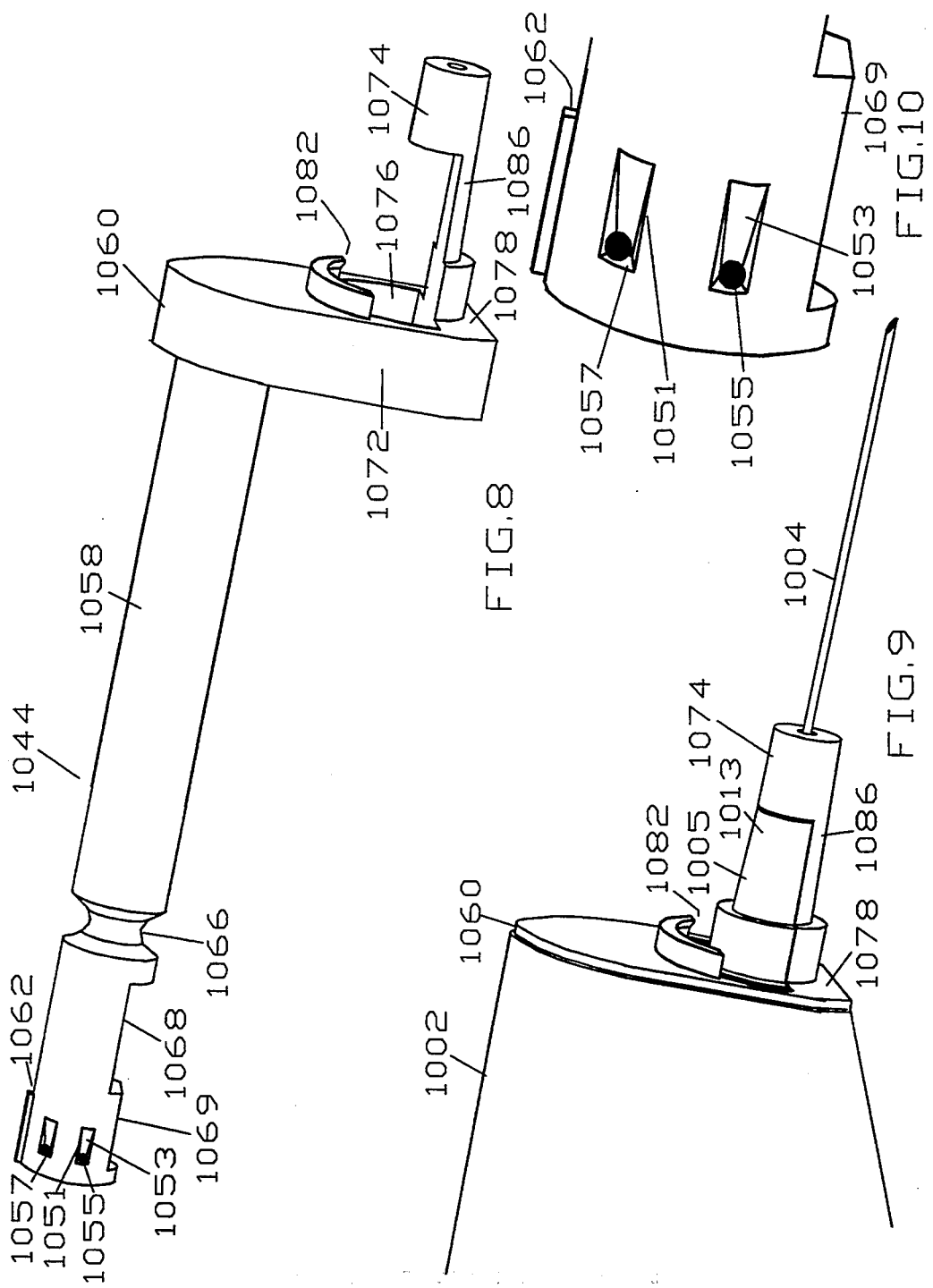

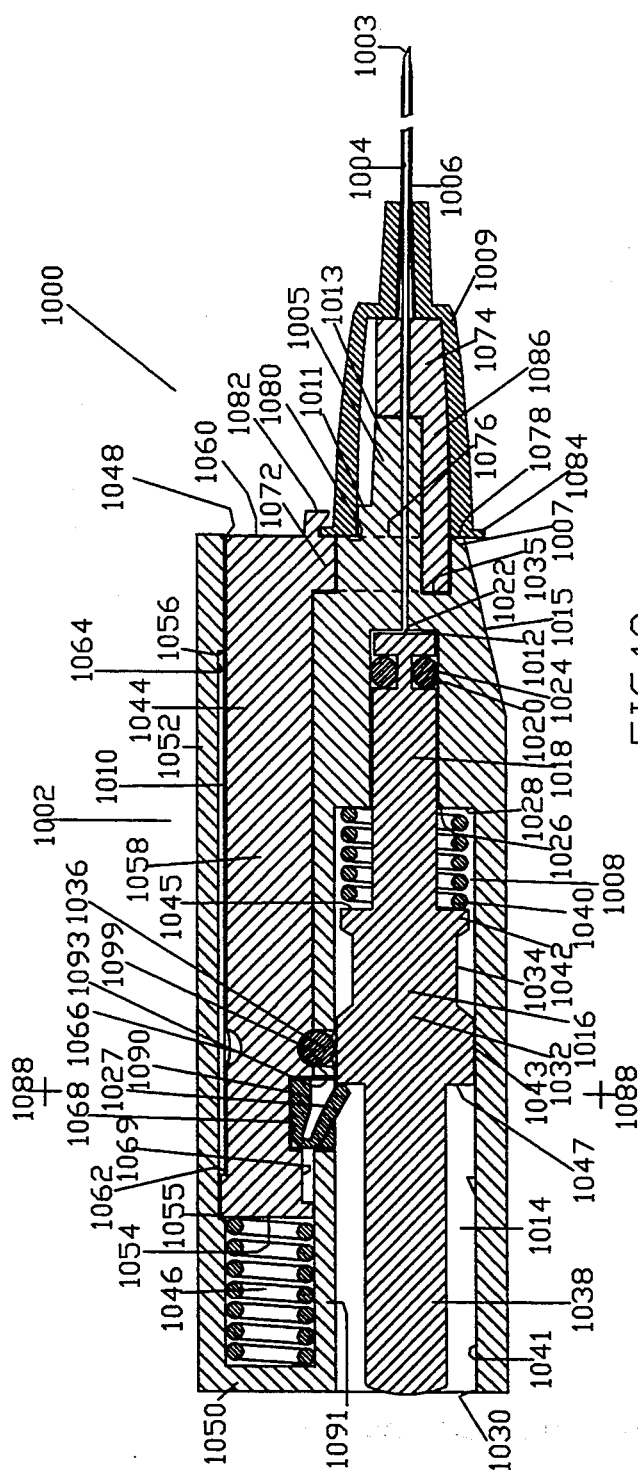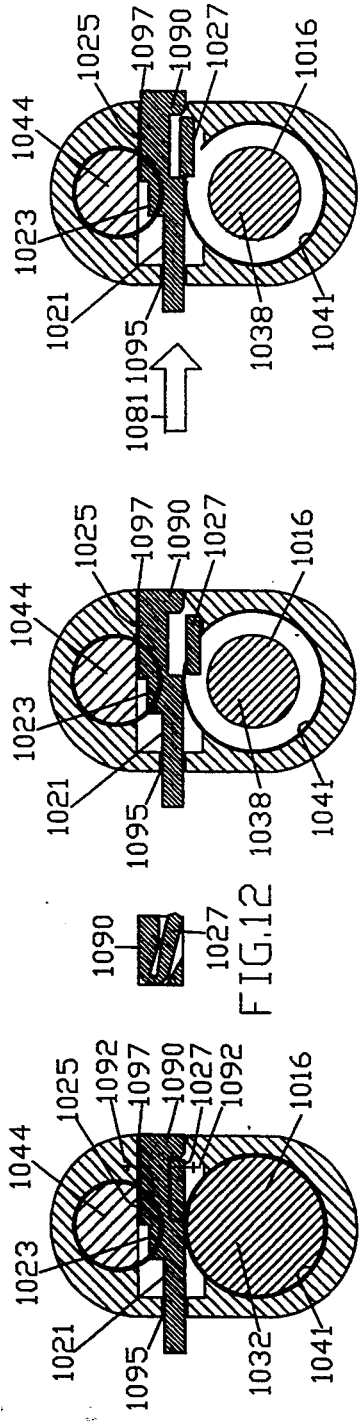

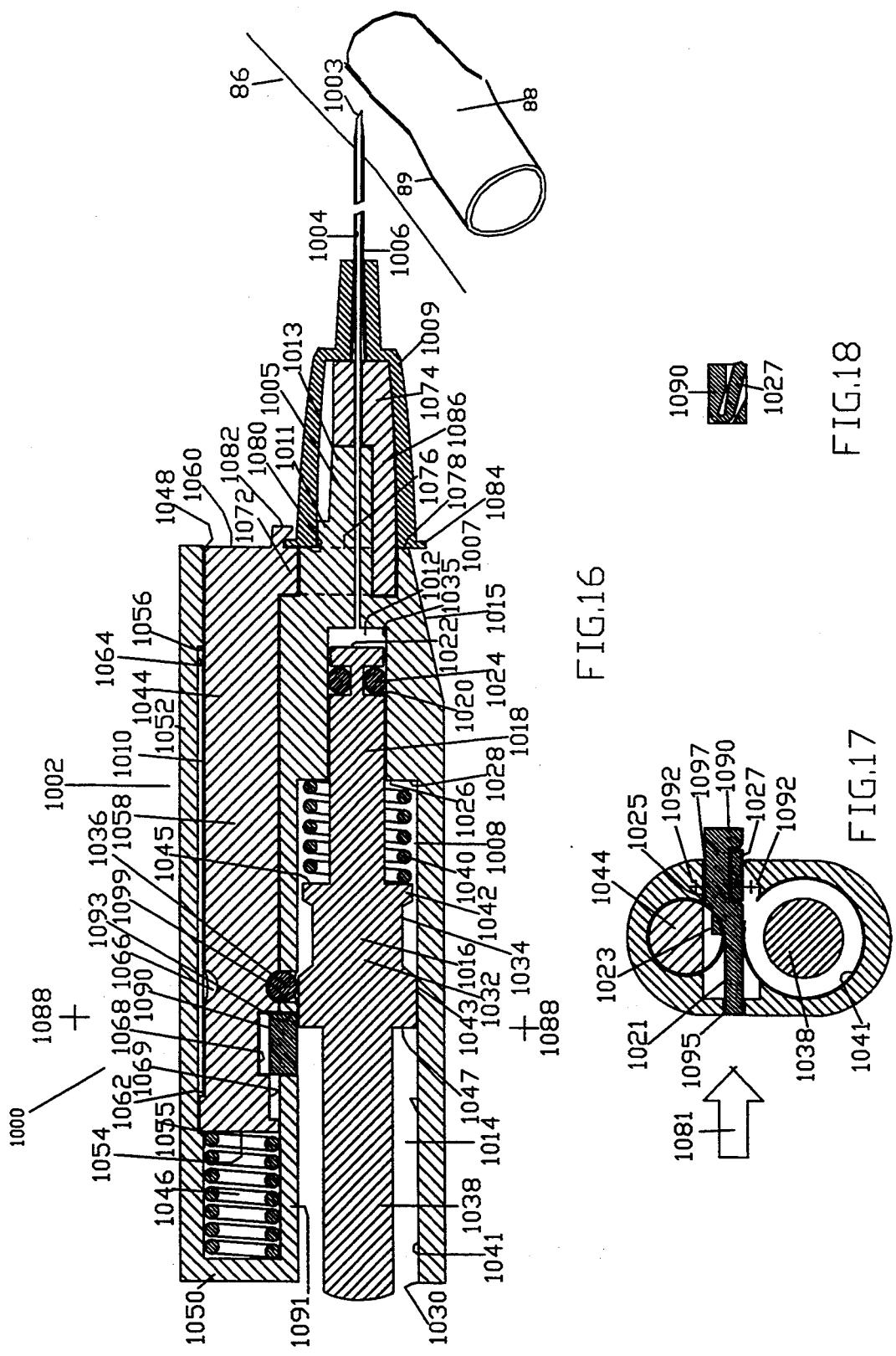

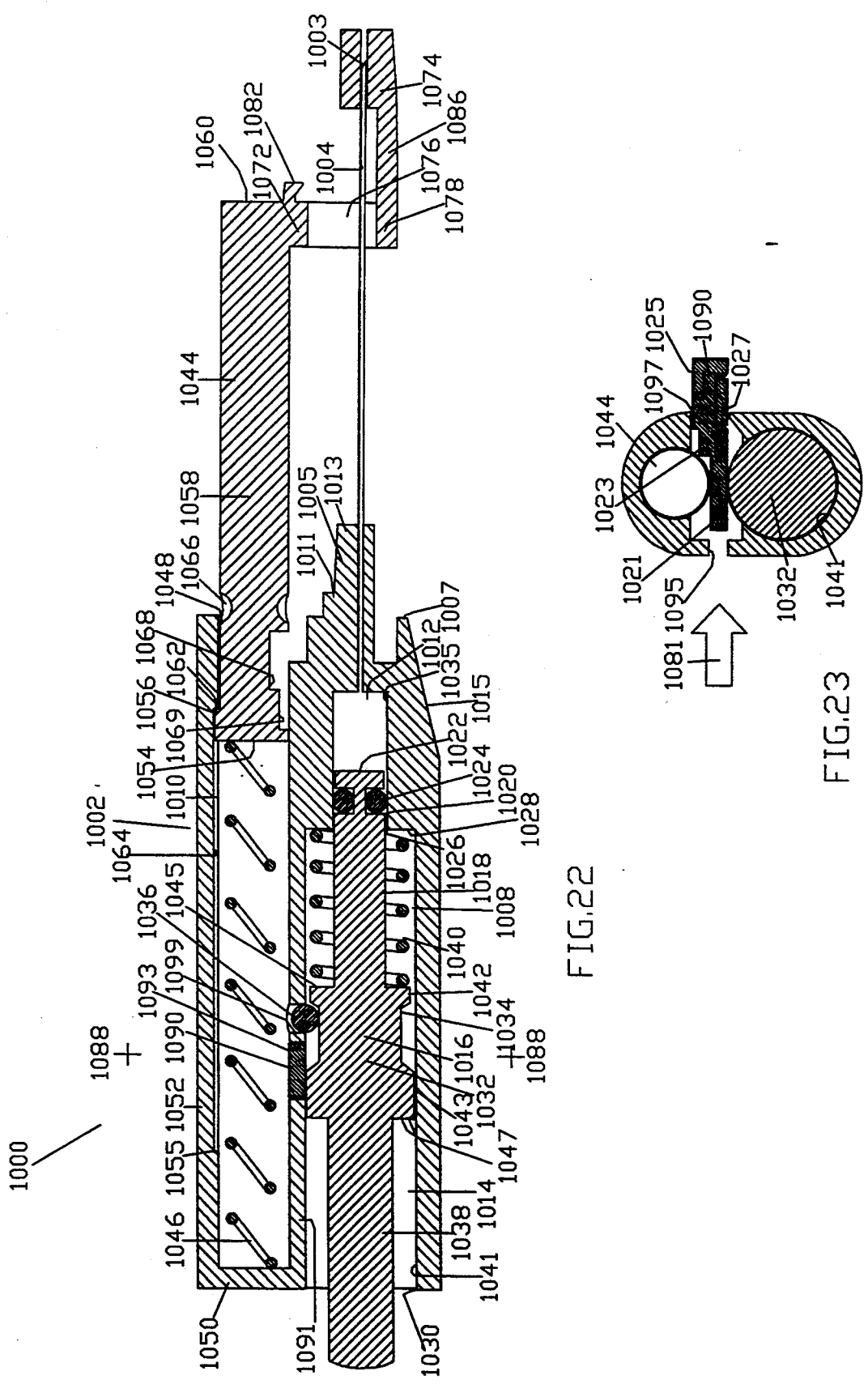

NEEDLE STICK PROTECTOR FOR AUTOMATIC CANNULATION DEVICES

BACKGROUND-FIELD OF INVENTION

This invention relates to accidental needle sticks protective devices, more specifically to needle sticks protecting devices applicable to the Automatic Cannulation Devices of patent application Ser. No. 07/929,182 filed on Aug. 10, 1992 and now U.S. Pat. No. 5,312,361.

BACKGROUND-DESCRIPTION OF PRIOR ART

Needle sticks among health care workers are not uncommon. Numerous diseases have been proved to be transmitted via needle sticks: hepatitis, malaria, siphylis, AIDS. Risks of transmission are inherent to the medical profession and prevention cannot be achieved only with heightened awareness, education or application of strict guidelines to avoid accidental needle stick punctures. Nothing could be more successful in reducing if not eliminating the risks of transmission of the above mentioned diseases than safe medical devices which prevent contacts of health care workers with contaminated sharps.

A search in the patent office revealed numerous protective devices for the exposed needle tip of hypodermic needles. Two are the basic types of needle sticks protecting devices.

In one type of devices the needle is retracted within a protective shield, manually or by resilient means. In the other group a sleeve or guard is described which is advanced over the needle manually or by resilient means. Locking of the sleeve or guard in respect to the needle and shielding of the needle tip is achieved in either group via various different mechanisms.

However no known protective mechanisms has been described for the Automatic Cannulation Device disclosed in our patent application Ser. No. 07/929/182 above mentioned.

BRIEF SUMMARY OF THE INVENTION

The unique characteristics of the Automatic Cannulation Device described in the above mentioned patent application demand unique solutions for the shielding of the needle tip of the Automatic Cannulation Device.

In all the embodiments of the Automatic Cannulation Device, an intravascular catheter concentric to a needle is automatically advanced over said needle upon blood vessel penetration by said needle by various means, including resilient means. Such an advancement is automatic in the sense that the intravascular catheter forward motion is self-initiated upon blood vessel penetration and self-sustained.

In some of the described embodiments of the Automatic Cannulation Device an interface member is interposed between the catheter and the resilient means.

In species of FIGS. 38 through 50 of the Automatic Cannulation Device of patent application Ser. No. 07/929,182, said interface member, interposed between the catheter and the resilient means, is described having the function of advancing the catheter over the needle with the purpose of cannulating a blood vessel. In carrying on the function of advancing the catheter over the needle, the interface member slides over the needle. When such an advancement is carried on for the full length of the needle and the interface member is locked in such a position, the interface member acts also as a needle protector.

The interface member of the embodiments of FIGS. 38 through 50 of patent application Ser. No. 07/929,182 is of a hollow generally cylindrical shape and concentric to the needle.

In another embodiment of said Automatic Cannulation Device, here newly described, the interface member is a solid rod parallel to the needle having a front portion interfacing with the catheter, said front portion being slideable over the needle with the purpose of advancing the catheter and covering the needle tip.

The interface member in either embodiments advances automatically in response to blood vessel penetration propelling said catheter forward into the interior of a blood vessel. Such an advancement is self initiated and does not require further intervention by the operator of the device after the blood vessel is penetrated by the needle tip.

The advancement of the interface member is self-initiated, being triggered by the vanishing of the vacuum within the vacuum chamber described in the Automatic Cannulation Device upon blood vessel penetration.

Shielding of the needle tip is therefore self-started and carried out automatically following penetration of the needle tip into a blood vessel.

The needle protection is completed by the locking of the interface member of the Automatic Cannulation Device in an advanced position for the purpose of needle tip shielding.

BRIEF DESCRIPTION OF THE DRAWINGS

FIG. 6 shows an alternative form of the device prior to use "out of the package", in cross section view.

FIG. 7 shows a cross section view of the device of FIG. 6 drawn at level of crosses 1088.

FIG. 8 shows a part of the device of FIG. 6, specifically the interface member.

FIG. 9 shows a detail of the device of FIG. 6, specifically the front end of the device.

FIG. 10 shows a detail of the interface member of FIG. 8, specifically the posterior end of the interface member illustrating the locking mechanism.

FIG. 11 is a cross section view of the device of FIG. 6, drawn at plane of cross signs 1088 showing the trigger during piston advancement, intermediate stage between the stage shown in FIG. 6 and FIG. 13.

FIG. 12 is a cross section of the trigger specifically of the trigger drawn at plane of cross signs 1092 of FIG. 11 showing the position of the resilient arrest of the trigger.

FIG. 13 is a cross section view of the device of FIG. 6 in a further stage, after full advancement of the piston, still prior to skin penetration.

FIG. 14 is a cross section view of the device of FIG. 13 at plane of crosses 1088 showing the position of the trigger, particularly of the resilient arrest of the trigger at completed piston advancement.

FIG. 15 is across section view of the device of FIG. 13 at plane of crosses 1088 showing the trigger in a further stage of operation.

FIG. 16 is a cross section view of the device of FIG. 6 in a further stage of operation, after skin penetration, but prior to blood vessel penetration.

FIG. 17 is a cross section view of the device of FIG. 16 at plane of crosses 1088.

FIG. 18 is a cross section view of a detail of FIG. 17 drawn at plane of crosses 1092 specifically showing the position of the resilient arrest of the trigger at the stage of operation shown in FIG. 16 and FIG. 17.

FIG. 22 shows the second step of the interface member advancement showing the interface member fully advanced with the needle tip enclosed by the guard.

FIG. 23 is a cross section view of the device of FIG. 22 showing the position of the trigger, section drawn at plane of crosses 1088.

OBJECTS OF THE INVENTION

Figure 1:
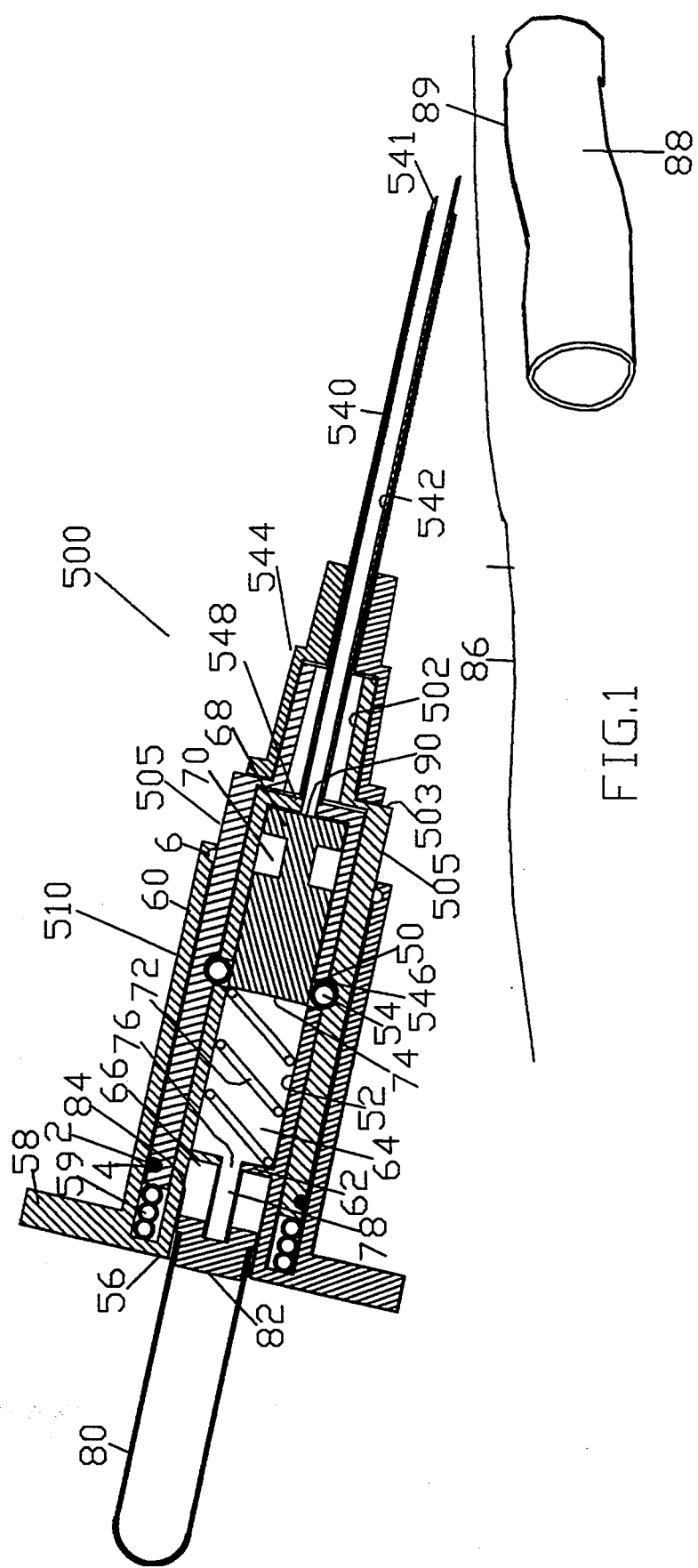
FIG. 1 shows the device in longitudinal cross section prior to skin penetration.

It is an object of the present invention to provide the Automatic Cannulation Device with a safe and effective method of needle tip protection.

It is also an object of the present invention to provide the Automatic Cannulation Device with an automatic needle protective mechanism, such a protective mechanism being self initiated upon blood vessel penetration and not requiring any intervention by the operator after blood vessel penetration.

It is also an object of our invention to provide the Automatic Cannulation Device with a needle tip protective mechanism that is simple to operate being actuable with only one hand.

It is an object of the present invention to provide the Automatic Cannulation Device with a needle protection which does not allow exposure of the needle tip to the environment at any time after tissue penetration.

It is also an object of the present invention to provide the Automatic Cannulation Device with a needle coverage mechanism that by not exposing the needle tip after tissue penetration, makes such a device a device totally free from contaminating exposures being the Automatic Cannulation Device a closed system device as the blood has no communication with the exterior once the blood vessel has been penetrated.

DESCRIPTION OF THE INVENTION

In the form of the present invention chosen for the purpose of illustration, a needle stick protective mechanism for the Automatic Cannulation Device of patent application Ser. No. 07/929,182 is shown in FIGS. 1, 2, 3 and 4.

The device 500 represented in FIGS. 1 to 4 is identical to the Automatic Cannulation Device 500 of FIG. 38 to 40 of patent application Ser. No. 07/929,182 with the addition of a locking expandable ring 2 forced within an annular groove 4 formed in the proximal portion of interface member 505 by cylindrical wall 60 of housing 510, and an annular groove 6 in the inner aspect of the distal portion of wall 60 of housing 510.

A brief summarized description of the Automatic Cannulation Device is here given along with a detailed description of the needle stick protective mechanism applied to it.

The device generally indicated at 500 is composed of five major components: an housing or propelling unit 510, a needle 542, a catheter 540, a vacuum capsule 80 and an interface member 505.

The generally cylindrically shaped housing 510 is composed of two concentric cylinders or cylindrical side walls, being 60 the outer cylindrical wall and 52 the inner cylindrical wall. Between the two cylindrical walls is harbored spring or resilient means 59. Inner cylindrical wall 52 has openings 50 for balls 54. Inner cylindrical wall 52 harbors piston 68 slideable in airtight fashion within said cylindrical wall 52. Piston 68 has annular recess 70 for reception of ball 54.

Vacuum capsule 80 with pierceable plug 82 is slideable within chamber 66 delimited laterally by sidewall 52 and anteriorly by wall member 62, having a central opening 76 on which posterior needle member 78 is mounted.

Spring 72 is interposed between wall member 62 and piston 68. Interface member 505, of generally cylindrical shape and slideably mounted between outer cylindrical wall 60 and inner cylindrical wall 52 of housing or propelling unit 510 has adaptor, or needle guard, 502 protruding from its front portion 503, said adaptor 502 being concentric to needle 542.

Figure 2:
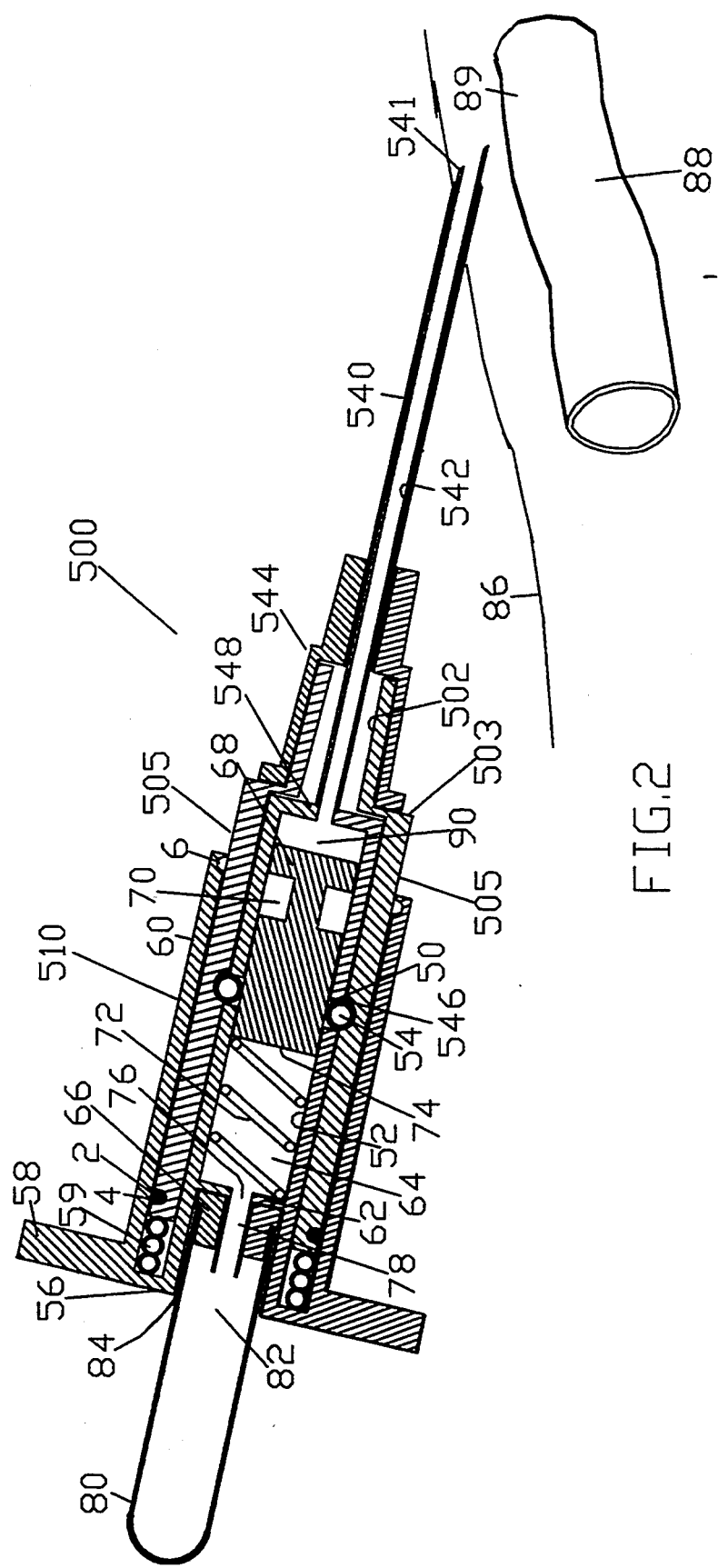
FIG. 2 shows the device in longitudinal cross section, armed after skin penetration but prior to blood vessel penetration.

In operation, as illustrated in FIG. 2, catheter placement device 500 is shown after tip 541 of needle 542 has penetrated skin 86 of a patient, but prior to penetration of a blood vessel 88. Once the tip 541 of needle 542 has entered the skin 86, the operator presses the vacuum capsule 80 forwardly, causing the post-needle member 78 to pierce plug 82. This causes air from chamber 64 of housing 510 to enter the capsule 80, creating a vacuum within the chamber 64 to partially retract piston 68 against the action of spring 72. This, in turn, creates a vacuum in space 90 forwardly of the piston 68. In this position of piston 68, the sidewalls of piston 68 still forces balls 54 into recess 70 to continue locking interface member 505 in its retracted position. The catheter placement device 500 is now "armed" to automatically advance the catheter 540.

Figure 3:
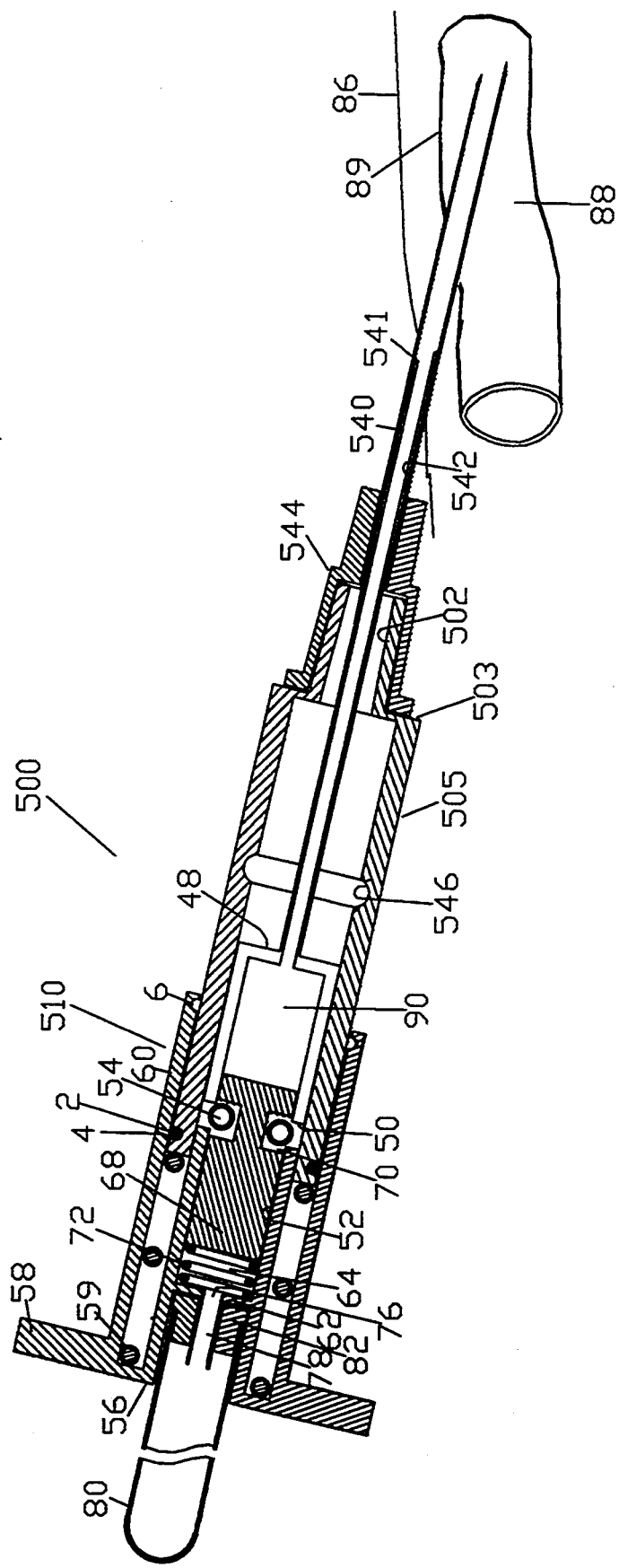
FIG. 3 shows the device in longitudinal cross section in process of actuation.

As shown in FIG. 3, needle tip 541 of needle 542 has penetrated wall 89 of the patient's blood vessel 88. The instant that such penetration occurs, blood from blood vessel 88 is drawn into space 90 in front of piston 68 by the vacuum present in space 90. This backflow of blood accelerated by the vacuum drives piston 68 rearwardly, against the action of spring 72, to the point that annular recess 70 of piston 68 becomes aligned with openings 50 of inner side walls 52. Consequently, balls 54 can move into recess 70 of piston 68 and out of recess 546 of interface member 505. When this occurs, spring 59 drives interface member 505 and consequently catheter 540 forwardly into blood vessel 88, automatically, without intervention by the operator.

Figure 4:
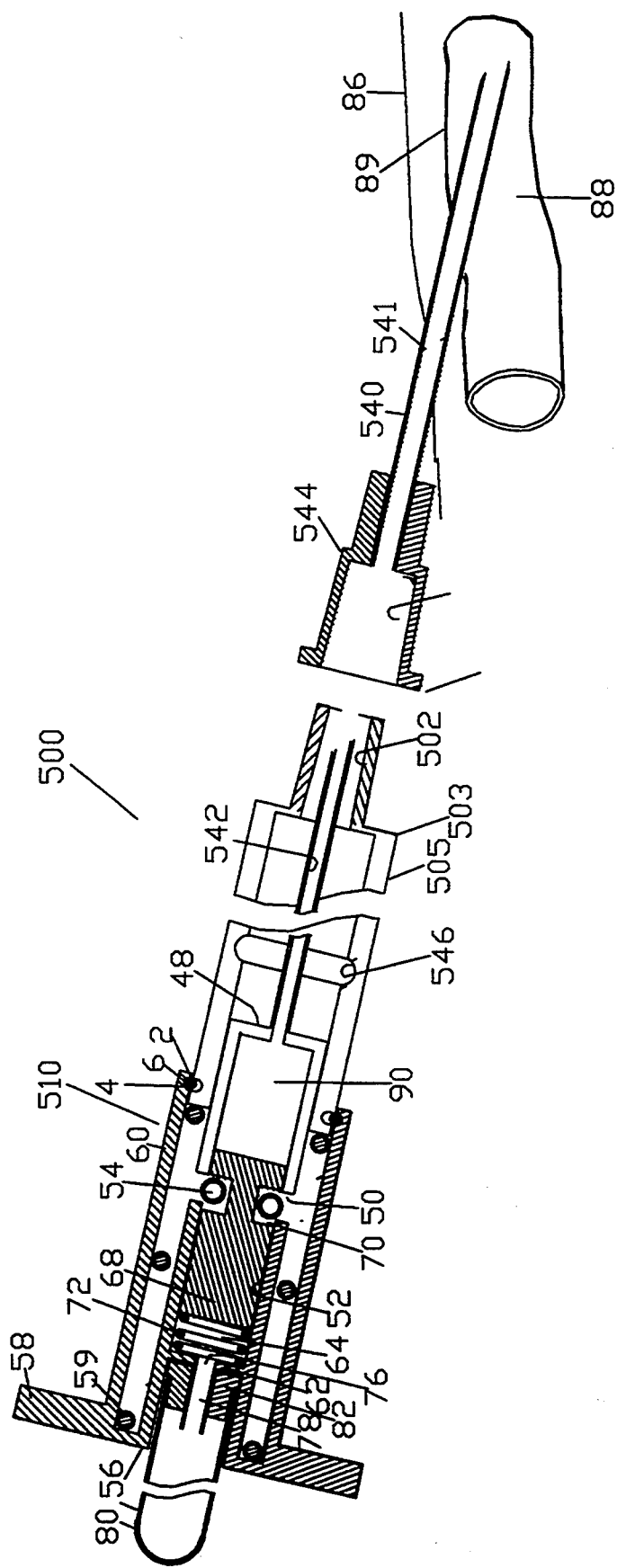
FIG. 4 shows the device in longitudinal cross section fully actuated with the needle tip fully covered.

As shown in FIG. 4, advancement of interface member 505 is arrested by the irreversible engaging of expanding ring 2, of round or preferably square cross section, into annular groove 6 of inner aspect of the distal portion of wall 60 of housing 510 when adaptor or needle guard 502 of front portion 503 of interface member 505 has passed needle tip 541 of needle 542. Needle 542 will therefore be encased in its entirety within interface member 505.

Such irreversible engagement of expanding ring 2 into annular groove 6 of outer wall 60 of housing 510 will irreversibly lock interface member 505 to housing 510 providing an automatic mechanism of needle shielding triggered by the vanishing of the vacuum.

Figure 5:
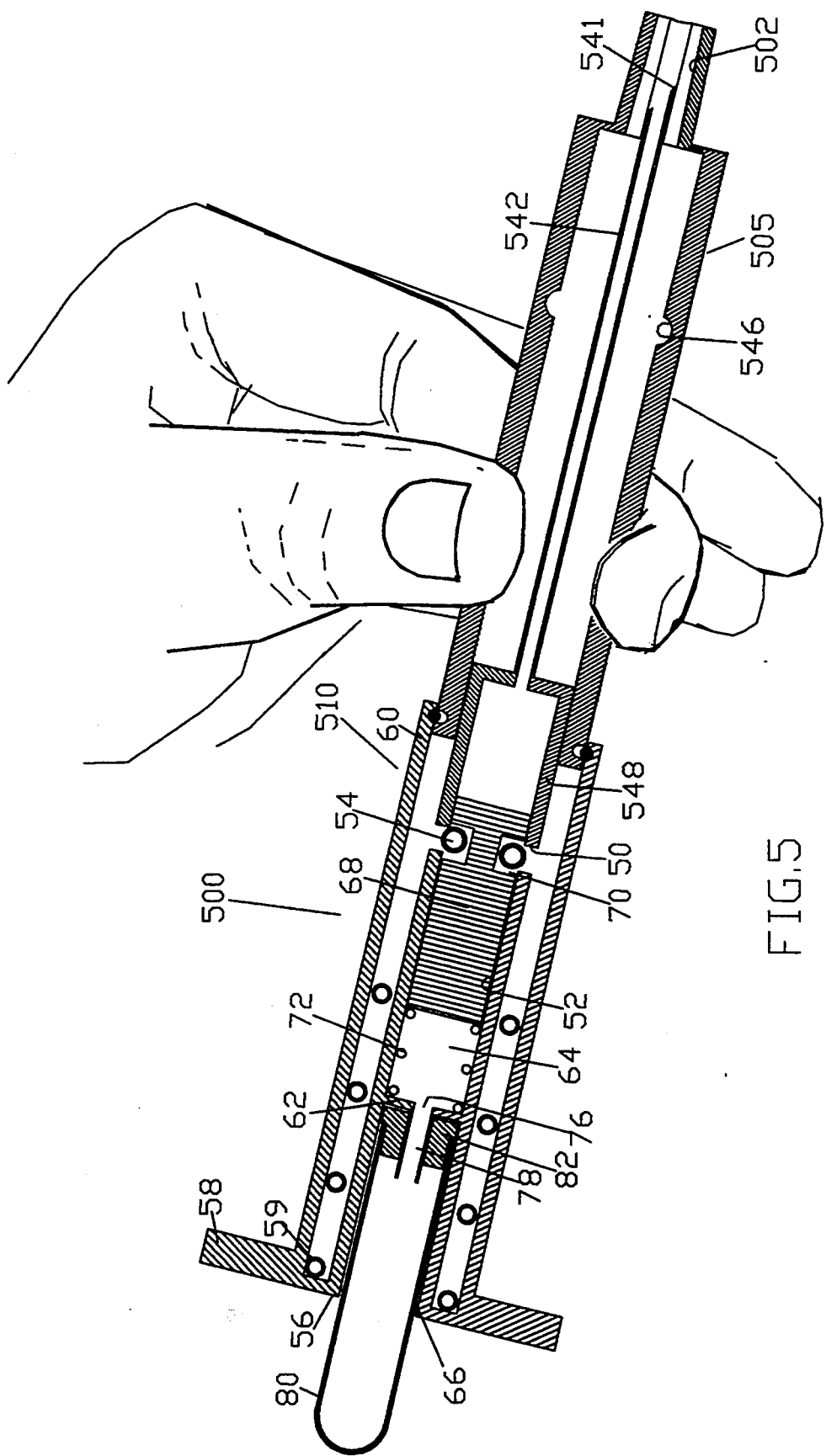
FIG. 5 is a cross section view of an alternative form of the device in which the interface member advancement accomplishing needle tip coverage is shown as a two steps procedure.

In FIG. 5 needle coverage by interface member 505 is achieved in two steps. The first step is an automatic advancement, triggered by the vanishing of the vacuum and carried out by self-propelling means to a predetermined length for the purpose of advancing the catheter to a predetermined length. The second step consists of further advancement of interface member 505 with its front portion 503 with adaptor or guard 502 beyond needle tip 541 of needle 540, and may be carried out by the same self-propelling means urging the interface member forward or may be carried out manually by the operator by the action of sliding forward interface member 505 until full coverage of needle tip 541 will ensue and locking of interface member 505 in respect of housing or propelling unit 510 will occur.

FIGS. 6 to 23 show an alternative form of the Automatic Cannulation Device of FIGS. 1 to 5 with an alternative form of interface member carrying an alternative form of needle stick protector or guard which, while preserving the general characteristics of being triggered by the vanishing of the vacuum occurring upon needle tip penetration of a blood vessel, differs from the needle stick protector described in FIGS. 1 to 5 for the mechanism locking the interface member in its extended position over the needle, said interface member being, in this alternative form, a solid rod having a front portion adapted to enclose the needle tip.

FIG. 6 is a cross section view through the device, generally indicated at 1000, prior to use. The device is composed of three main parts: a propelling unit or housing 1002, a needle 1004, and a catheter 1006.

Propelling unit or housing 1002 is composed of two parallel chambers of generally cylindrical shape: piston chamber 1008 and interface member chamber 1010.

Propelling unit or housing 1002 is connected to needle 1004 via needle hub 1005 which protrudes from anterior end 1007 of housing 1002. Needle hub 1005 has base 1011 which precisely fits within catheter hub 1009 of catheter 1006, and nozzle 1013 in continuity with said base 1011 to allow adequate leeway for catheter hub 1009 of catheter 1006 when catheter 1006 is in an advanced position, as it will be described in the description of the operation.

Piston chamber 1008, delimited laterally by sidewall 1041, is composed of an anterior or vacuum chamber 1012 in communication with hollow needle 1004, and a posterior chamber 1014 of larger diameter than vacuum chamber 1012. Posterior chamber 1014 is in continuity of vacuum chamber 1012 via opening 1026, with collar 1028 encircling opening 1026. Posterior chamber 1014 is open posteriorly via opening 1030.

In piston chamber 1008 is slideably mounted piston 1016. Piston 1016 is composed of three segments: an anterior segment 1018, which is partially contained in vacuum chamber 1012 and partially in posterior chamber 1014. The anterior segment 1018 of piston 1016 has an annular groove 1020 formed in proximity of its front portion 1022, where O-ring 1024 is mounted in airtight fashion with wall 1035 of vacuum chamber 1012. The intermediate segment 1032 of piston 1016, is in continuity with anterior piston segment 1018, is of larger diameter than anterior piston segment 1018 to fit in chamber 1014 of larger diameter. Intermediate segment 1032 has a front face 1045, a posterior face 1047 and a side face 1043. On said side face 1043 is a wide annular recess 1034 for ball member 1036 as it will be explained below, and flange 1042. Spring 1040 is mounted around anterior segment 1018, between collar 1028 and flange 1042 of intermediate piston segment 1032. Posterior piston segment 1038, in continuity with intermediate piston segment 1032, extends posteriorly through opening 1030 of chamber 1008.

Interface member chamber 1010 of generally cylindrical shape is delimited laterally by wall 1052, is open anteriorly via opening 1048 and closed posteriorly by posterior wall 1050. Within chamber 1010 is slideably mounted interface member 1044. Spring 1046 is also contained in interface member chamber 1010, posteriorly to interface member 1044.

Side wall 1052 of chamber 1010 is formed with longitudinal groove 1064 extending from posterior end 1055 up to arrest 1056 anteriorly.

As best seen in FIG. 8, interface member 1044 of generally cylindrical shape to fit chamber 1010, is composed of a body segment 1058, and a front portion 1060.

Body 1058 has arrest tooth 1062 slideable, as shown in FIG. 6, within groove 1064 of side wall 1052 up to arrest 1056. Interface member 1044, as shown in FIG. 8, is also formed with annular recess 1066 for ball member 1036 and deep notch 1068 and a shallow contiguous notch 1069 for trigger 1090 as it will be described below in details.

As best seen in FIG. 10, interface member 1044 has, at its posterior end, locking means 1051, composed of slanted slots 1053, housing balls 1055, which, in position of rest, prior to use seat posteriorly in recess 1057 of slanted slots 1053.

Front portion 1060 of interface member 1044, as best shown FIG. 8 and FIG. 9, is composed of a propelling sleeve or needle guard 1074 connected to body 1058 of interface member 1044 via arm or plate 1072. Arm or plate 1072 has opening 1076 to accommodate needle hub 1005, a seating 1078 adapted to base 1080 of catheter hub 1009 and hook 1082 to releasably engage flange 1084, which is shown in FIG. 6, of catheter hub 1009. As shown in FIGS. 8 and 9, propelling sleeve or needle guard 1074 of generally cylindrical shape in order to fit within catheter hub 1009 in front of needle hub nozzle 1013 and attached to arm 1072 via bridge 1086, is slideable over needle 1004.

As shown in FIG. 6, within chamber 1010, between posterior wall 1050 of chamber 1010 and posterior end 1054 of interface member 1044 is propelling means or spring 1046.

As shown in FIG. 6, chamber 1010 and chamber 1008 are separated for the whole length by divider wall 1091.

A window 1099 is formed in the divider wall 1091 to house ball member 1036.

In FIG. 6 ball member 1036 is shown protruding from window 1099 of divider wall 1091 and seating in recess 1034 of piston 1016 and not engaged in correspondent annular recess 1066 of interface member 1044.

As best shown in FIG. 6 and in FIG. 7, which is a cross section representation of the device at level of crosses 1088 of FIG. 6, chamber 1008 and chamber 1010 share lateral opening 1095 on one side and 1097 on the opposite side and divider wall 1091 in correspondence of said openings is interrupted in order to house trigger 1090 to engage both chambers. As shown in cross section view in FIG. 7, trigger 1090 has multiple indentation levels, 1021, 1023 and 1025 adapted to releasably engage both piston 1016 and interface member 1044 at different operational stages, as it will be illustrated in the description of operations. Arrest 1027 of trigger 1090 located in correspondence of indentation level 1025 protrudes into piston chamber 1008.

In position of rest, prior to use, interface member 1044 is locked in its starting position by indentation 1025 engaging deep notch 1068 of interface member 1044.

Propelling unit or housing 1002 has a slant 1015 in its antero-inferior segment to facilitate the insertion of needle 1004.

Hollow needle 1004 has a tip 1003 and protrudes from hub 1005 which has been previously described.

Catheter 1006 with hub 1009 is slideably mounted over needle 1004 and its hub 1005.

DESCRIPTION OF THE OPERATIONS

As shown in FIG. 13, the operator will first advance piston 1016 within chamber 1008 by applying forward pressure on posterior piston segment 1038 with the purpose of overcoming the breakout friction of O-ring 1024. In so doing, the operator will load spring 1040 encircling anterior segment 1018 of piston 1016, said spring 1040 acting between collar 1028 of posterior chamber 1014 and flange 1042 of intermediate piston segment 1032.

FIG. 11, a cross section view of device 1000 drawn at plane of cross signs 1088 of FIG. 13, and FIG. 12, a cross section view of trigger 1090 drawn at plane of cross signs 1092 of FIG. 11, show the position of the resilient arrest 1027 of trigger 1090 during such piston advancement.

FIG. 14, another cross section view of device 1000 drawn at plane of cross signs 1088 of FIG. 13, shows the position of the resilient arrest 1027 of trigger 1090 at completed piston advancement.

Trigger 1090, as shown in FIG. 15, another cross section view of device 1000 drawn at plane of cross signs 1088 of FIG. 13, is then pushed sideways by the operator to align, as seen in FIG. 13, its arrest 1027 with posterior face 1047 of intermediate segment 1032 of piston 1016 to engage and lock piston 1016 from moving backward by the action of the just loaded spring 1040 acting between collar 1028 of posterior chamber 1014 and flange 1042 of intermediate piston segment 1032. As seen in FIG. 13, this anterior displacement of piston 1016 will also cause ball member 1036 to move from recess 1034 of piston 1016 onto side face 1015 of intermediate segment 1032 of piston 1016 through window 1099 of divider wall 1091 to protrude into annular recess 1066 of interface member 1044 to releasably engage and lock interface member 1044.

In a following stage, shown in FIG. 16 and in FIG. 17, another cross section view of device 1000 drawn at plane of cross signs 1088 of FIG. 16 the operator, after inserting the needle tip 1003 under the skin 86 in an area of a visible blood vessel or of an expected blood vessel location, arms the device by pushing trigger 1090 sideways, as seen in FIG. 17, in direction of arrow 1081 to align indentation 1023 to disengage both piston 1016 and interface member 1044, free now to be displaced, as shown in FIG. 16.

FIG. 18, a cross section view of trigger 1090 drawn at plane of cross signs 1092 of FIG. 17, shows a view of the position of resilient arrest 1027 of trigger 1090 at this stage of the operations.

As seen in FIG. 16., piston 1016, now free to be rearwardly displaced, is only partially rearwardly displaced by the partial extension of loaded spring 1040, due to the sealing properties of the subcutaneous tissue. Due to the same sealing properties of the subcutaneous tissue, a vacuum is created in vacuum chamber 1012 in front of anterior segment end 1022 of piston 1016 by said rearward displacement of piston 1016: said vacuum will act as a retaining force upon piston 1016 opposing the rearward displacement of piston 1016 urged backward by loaded spring 1040. As a result of said partial rearward displacement of piston 1016, recess 1034 of intermediate piston segment 1032 approaches window 1099 of divider wall 1091 where ball member 1036 is located, but does not quite align with said window 1099. Ball member 1036, housed in said window 1099, not aligned yet with recess 1034 of intermediate piston segment 1032 is held by side face 1043 of intermediate piston segment 1032 in window 1099 of divider wall 1091, and protrudes into recess 1066 of interface member 1044 so to lock said interface member 1044 to housing 1002 and prevent it from advancing by action of loaded spring 1046 urging forward said interface member 1044.

The device is then further advanced by the operator toward a blood vessel. During said advancement, hook 1082, as shown in FIG. 16, maintains its engagement with flange 1084 of catheter hub 1009 and retains catheter 1006 firmly attached to the device, not allowing separation of the catheter hub 1009 from the front portion 1060 of the interface member 1044 even in case of withdrawal of the device.

Figure 19:
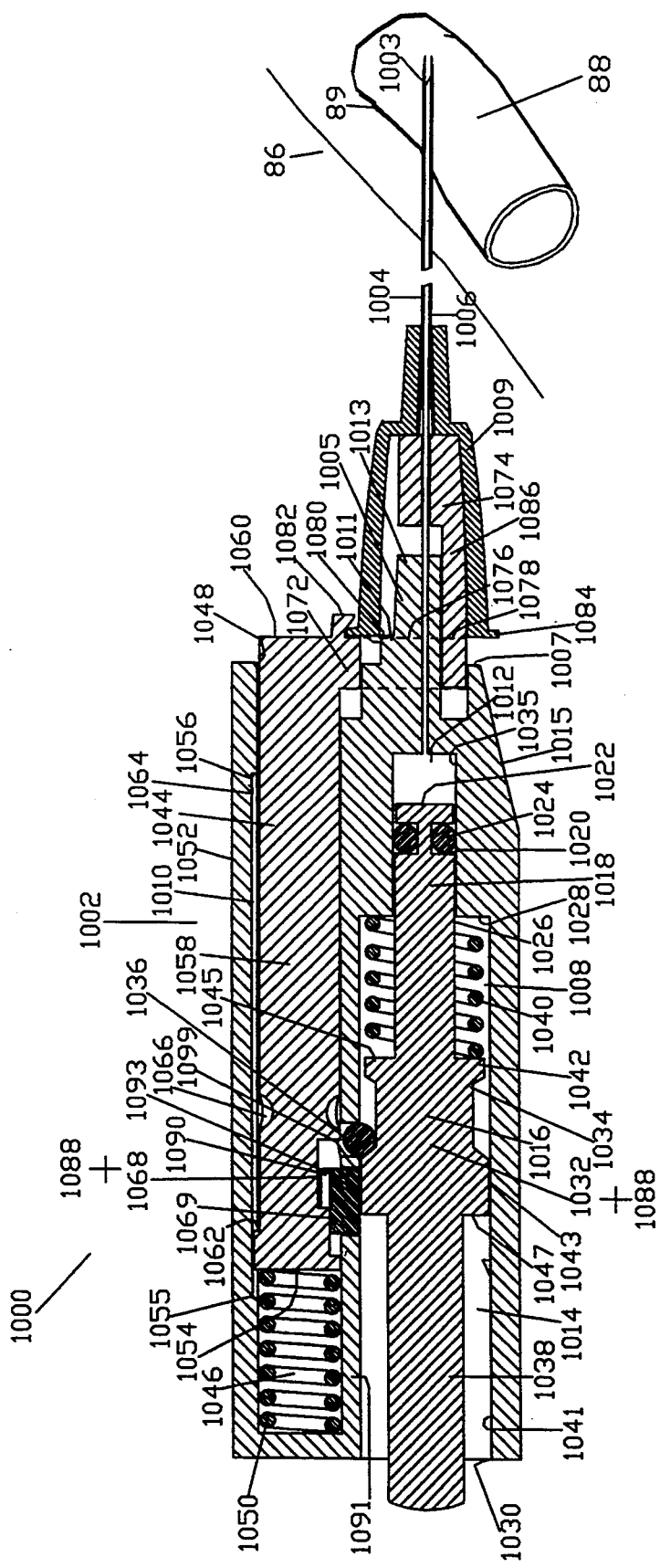
FIG. 19 shows in cross section the device of FIG. 6 in a further stage of operation, just after blood vessel penetration by the needle tip showing the initial advancement of the interface member.

In a following stage, as shown in FIG. 19, as soon as needle tip 1003 will penetrate the wall 89 of blood vessel 88, blood will rush into vacuum chamber 1012 through hollow needle 1004, causing the vanishing of the vacuum in vacuum chamber 1012 and allows further posterior displacement of piston 1016 to the point that ball member 1036 will align with recess 1034 of intermediate piston segment 1032 allowing ball member 1036 to fall into recess 1034 of piston 1016, its protruding portion being urged to exit annular recess 1066 of interface member 1044 by propelling means or interface member loaded spring 1046.

Interface member 1044, no longer retained by ball member 1036, will be propelled forward by propelling means 1046, pushing forward catheter 1006 via seating 1078 of arm or plate 1072 adapted to base 1080 of catheter hub 1009 and via propelling sleeve 1074.

Hook 1082 continues to engage with flange 1084 of catheter hub 1009 for a limited predetermined amount of advancement of interface member 1044 while catheter hub 1009 slides over base 1011 of needle hub 1005 due to the fact that base 1011 fits exactly within catheter hub 1009 in a way to prevent radial leeway and consequent disengagement of flange 1084 of catheter hub 1009 from hook 1082 of arm or plate 1072.

Figure 20:
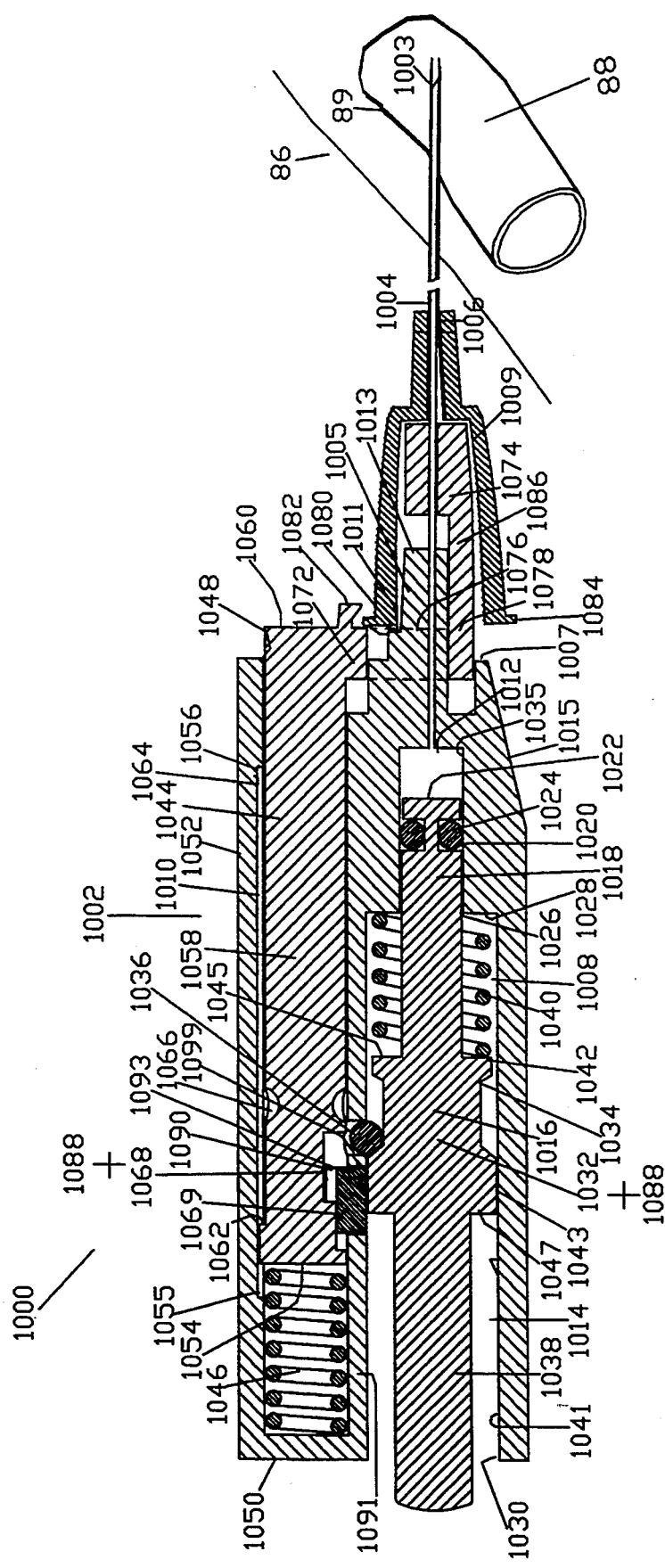
FIG. 20 shows in cross section the device of FIG. 6 in a further stage of operation showing a further advancement of the interface member.

As shown in FIG. 20, when catheter hub 1009 is further advanced over nozzle 1013 of needle hub 1005, adequate radial leeway is allowed to catheter hub 1009 to disengage from hook 1082 of arm or plate 1072, permitting disengagement of catheter 1006 from propelling unit 1002.

Figure 21:
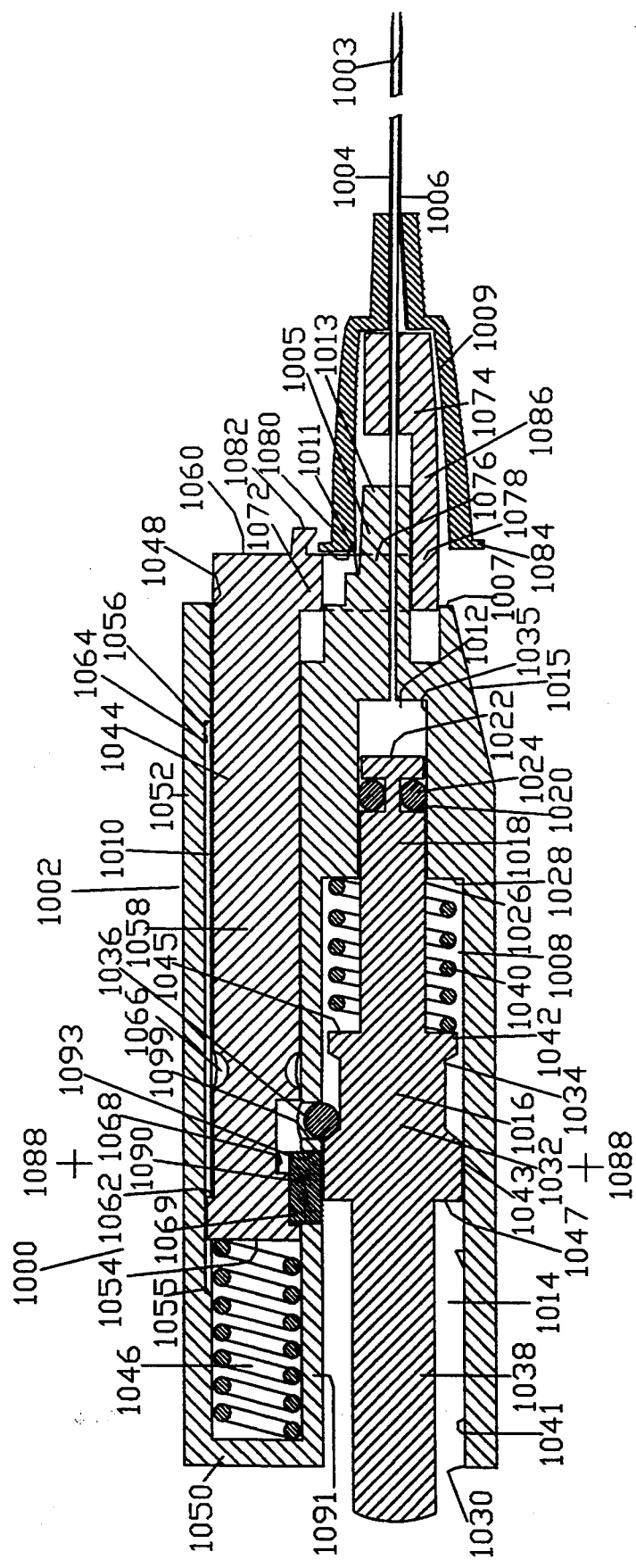
FIG. 21 shows in cross section the device of FIG. 6 in a further stage of operation showing the maximum permitted advancement of the interface member as single uninterrupted step.

Interface member advancement, in this version of the device, as seen in FIG. 21, will be permitted only for a predetermined amount by the engagement of indentation 1023 shown in FIG. 17, of trigger 1090 with shallow notch 1069 of interface member 1044, as shown in FIG. 21.

The enclosing of needle tip 1003, as shown in FIG. 22, by propelling sleeve or needle guard 1074 for the purpose of protection from needle sticks is simply accomplished by further sideways displacement of trigger 1090 in direction of arrow 1081, as shown in FIG. 23, to align indentation 1021 of trigger 1090 with shallow notch 1069, FIG. 22, of interface member 1044, thereby releasing interface member 1044 for further self-propelled advancement.

Arrest of propelling sleeve or needle guard 1074 in advanced position beyond needle tip 1003 for the purpose of needle tip shielding is achieved by locking means 1051 previously described and arrest tooth 1062.

Engagement of arrest tooth 1062 of interface member 1044 on arrest 1056 of longitudinal groove 1064 will not permit further forward advancement of intermediate member 1044 or eventual exit of interface member 1044 from interface member chamber 1010. Locking means 1051 will not permit posterior displacement of interface 1044 in respect to housing 1002 by the irreversible wedging of balls 1055 between slanted slots 1053 and side wall 1052 of interface member chamber 1010.

The enclosing of needle tip by the propelling sleeve or needle guard of the interface member for the purpose of protection from needle sticks may also be manually accomplished by manual forward sliding of interface member, after advancement of catheter by self-initiated automatic advancement of interface member to a predetermined length, in response to vanishing of the vacuum as described above.

Figure 24:
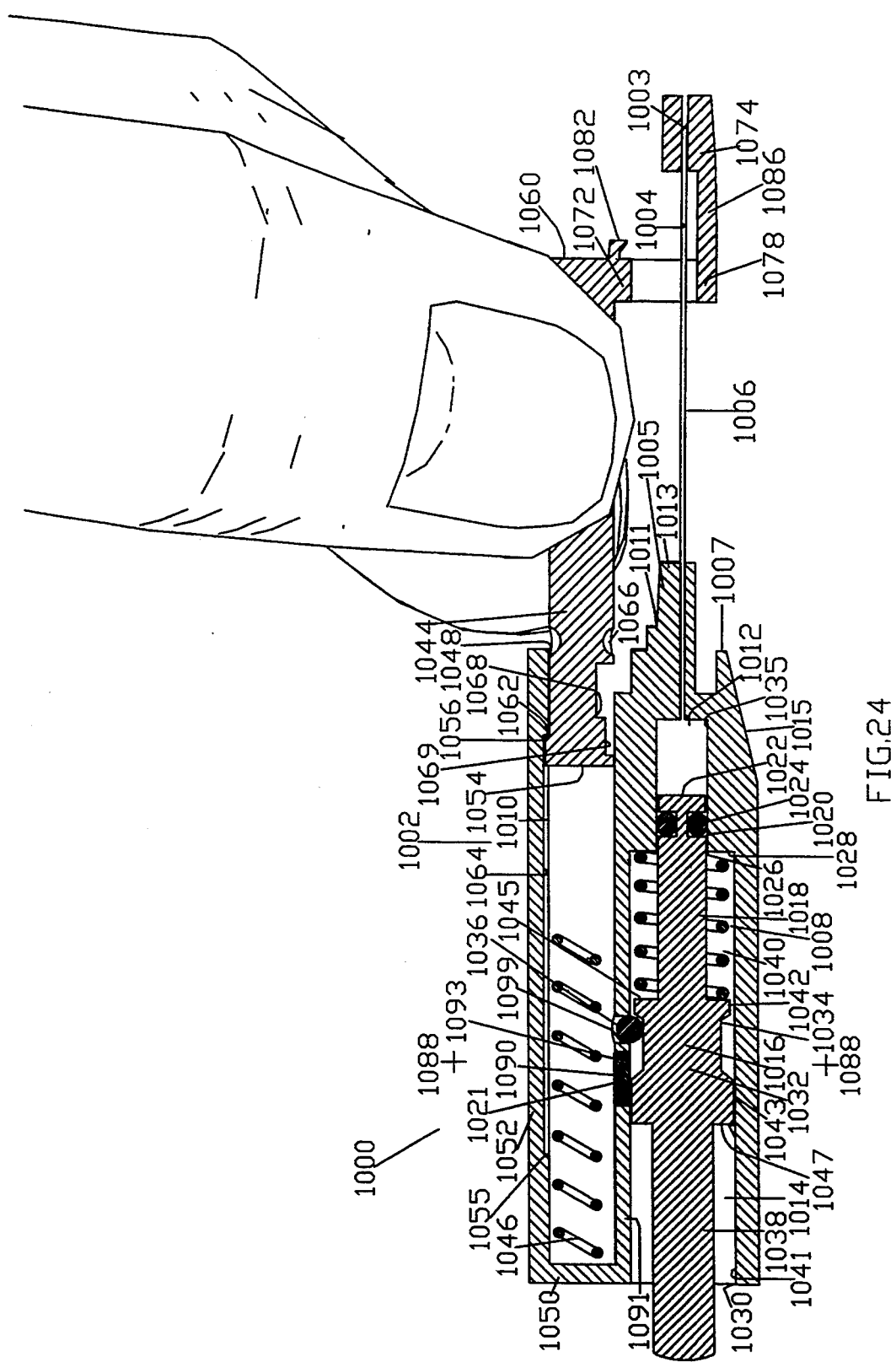
FIG. 24 is a cross section view of another version of the device of FIG. 6 showing needle tip enclosing by the needle guard being accomplished manually by the operator by sliding forward the interface member after the initial predetermined automatic advancement of the interface member.
Figures 25, 26:
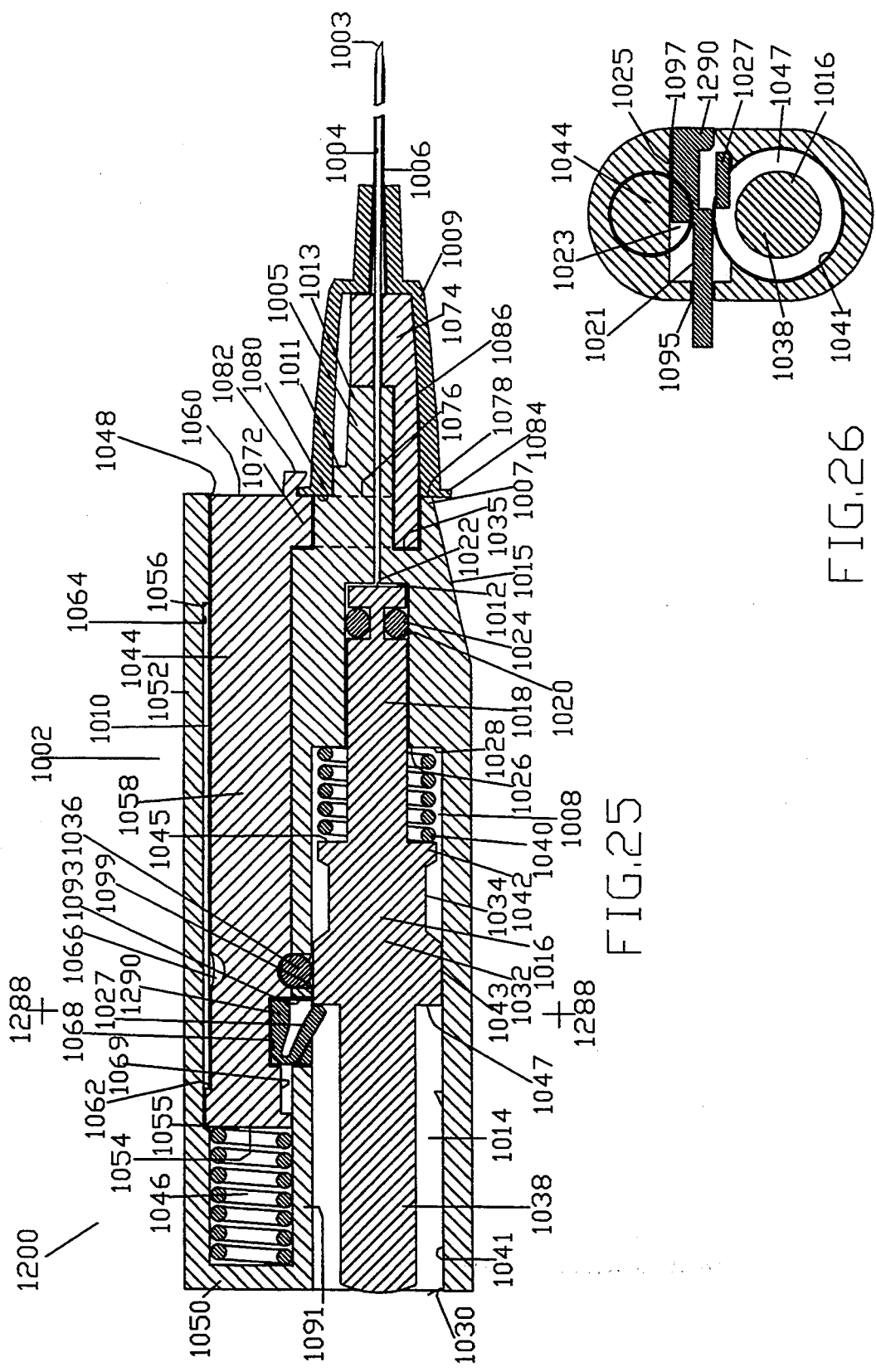
FIG. 25 is a cross section view of another version of the device of FIG. 6.
FIG. 26 is a cross section view of the device of FIG. 25 drawn at plane of crosses 1288.
Figures 27, 28:
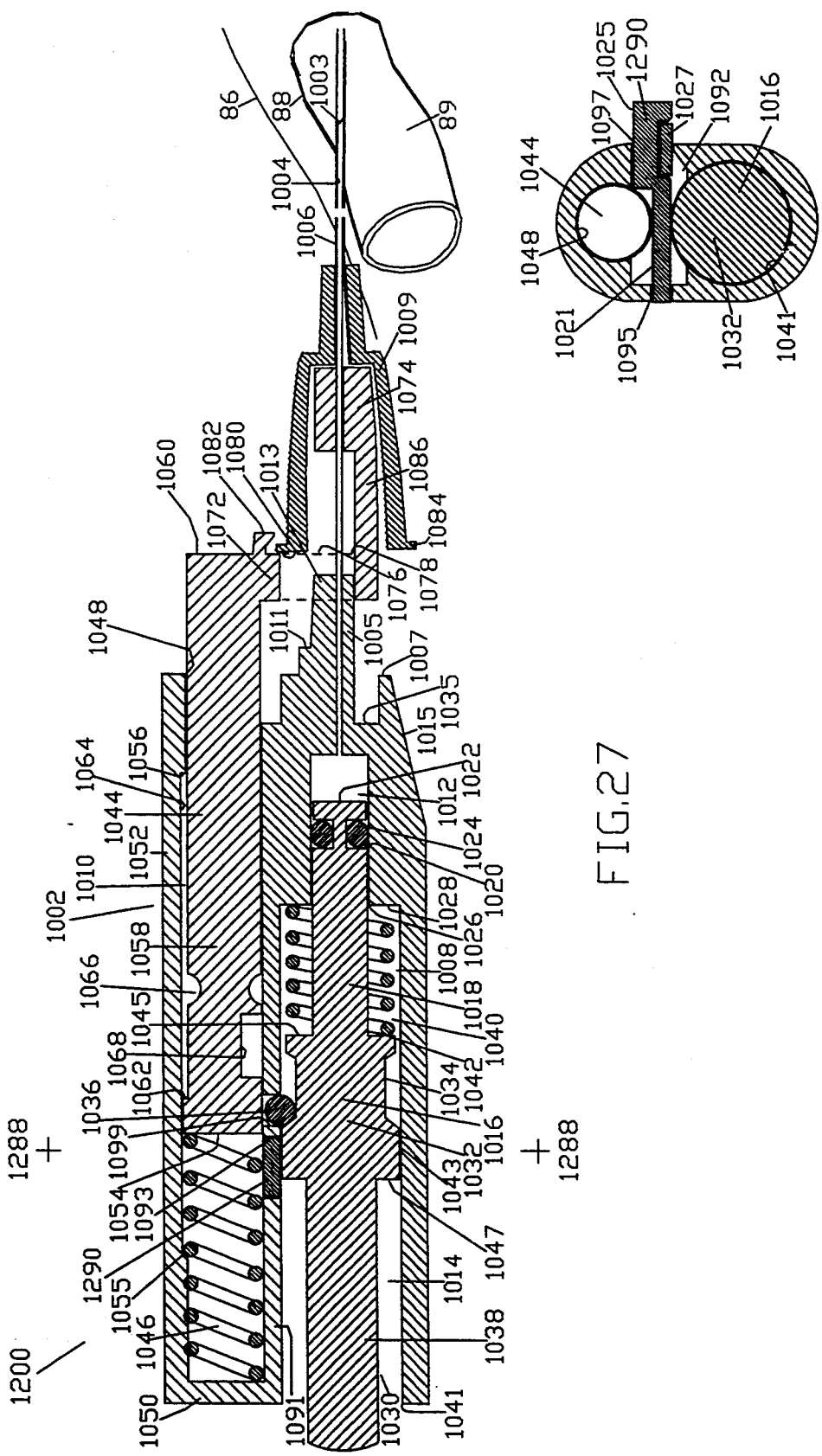
FIG. 27 is a cross section view of the device of FIG. 25 shown after blood vessel penetration by the needle tip.
FIG. 28 is a cross section view of the device of FIG. 27 drawn at plane of crosses 1288.
Figure 29:
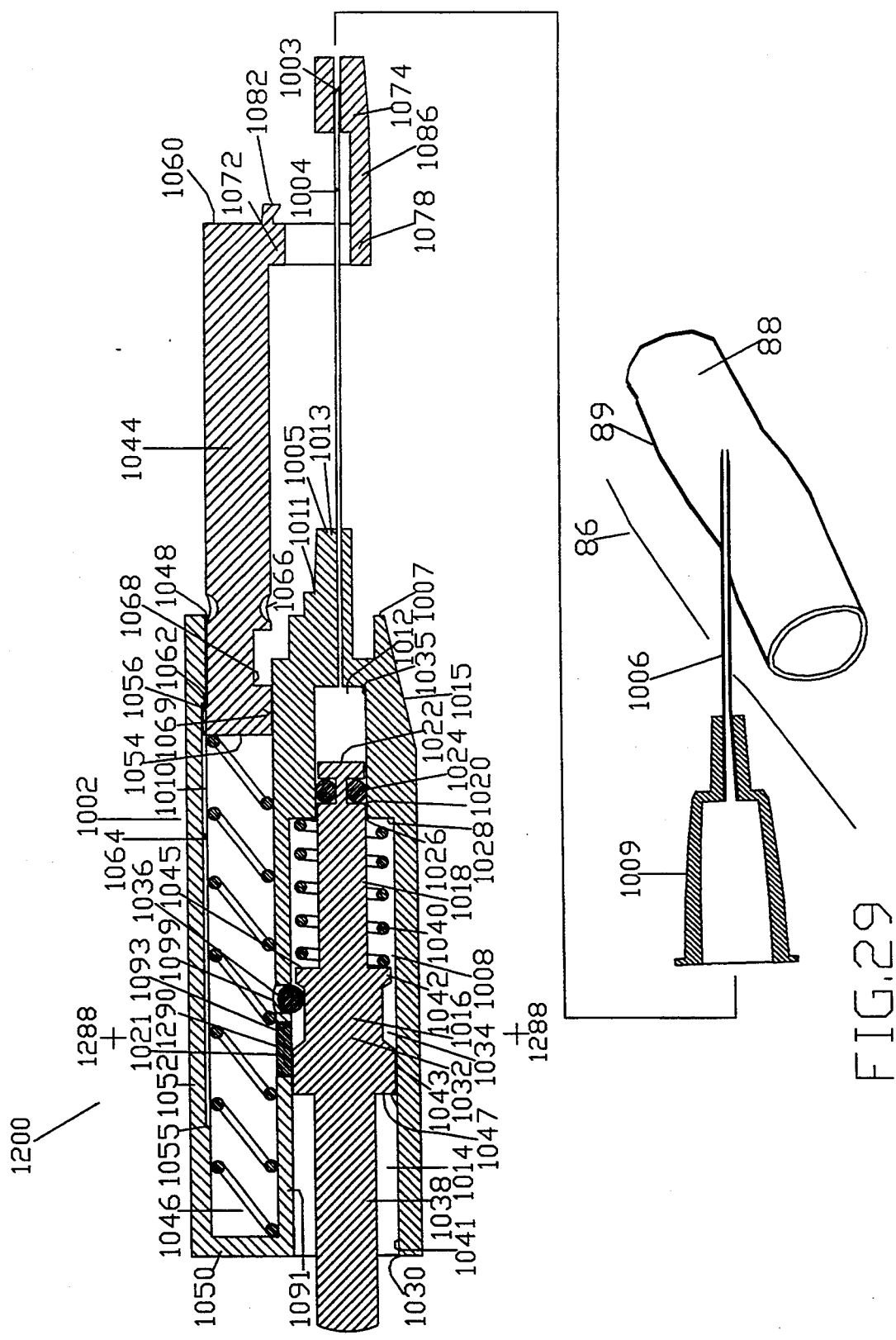
FIG. 29 shows the device of FIG. 25 in cross section showing full advancement of the interface member accomplished as a single uninterrupted step.

FIG. 24 shows this manual advancement of the interface member 1044 to cover needle tip 1003 with needle guard 1074 for the purpose of needle tip protection against accidental needle sticks, being accomplished after release of interface member 1044 occurring as a result of sideways displacement of trigger 1090, as best shown in FIG. 23, in direction of arrow 1081 to align indentation 1021 of trigger 1090 with shallow notch 1069 of interface member 1044, thereby releasing interface member 1044 for further manual advancement.

Arrest of propelling sleeve or needle guard 1074 in advanced position beyond needle tip 1003 for the purpose of needle tip shielding and locking of needle guard 1074 to protect needle tip 1003 is achieved by the same mechanism as for device 1000 of FIGS. 6 to 23.

The catheter advancement by the interface member and the needle tip enclosing by the needle guard for the purpose of needle tip protection may also be accomplished in a single step, instead of been accomplished in two steps as in the previously described versions of the device, by a minimal change in the trigger configuration of indentations as well different notch configuration of interface member.

FIGS. 25, 26, 27, 28 and 29 show this alternative form, generally indicated at 1200, of the device 1000 of FIGS. 6 to 23, in all similar to device 1000 except, as mentioned above, for differences in the configuration of indentations of trigger 1090. Trigger 1290 of FIG. 26, a cross section of device of FIG. 25, drawn at plane of cross signs 1288 of FIG. 25, has two levels of indentations, 1221 and 1225, with absence of indentation corresponding to 1023 of trigger 1090. Notch 1069 of interface member 1044 of device 1000 is no longer present in interface member 1244 of device 1200.

As a result of this respective configuration, in use, the operational steps of device 1200 are the same as the operational steps of device 1000 except that interface member 1244 is fully advanced by spring 1246 to enclose needle tip in a continuous fashion following cannulation of catheter 1006, in response to vanishing of the vacuum occurring automatically in response to penetration of wall 89 of blood vessel 88 by needle tip 1003.

Figure 30:
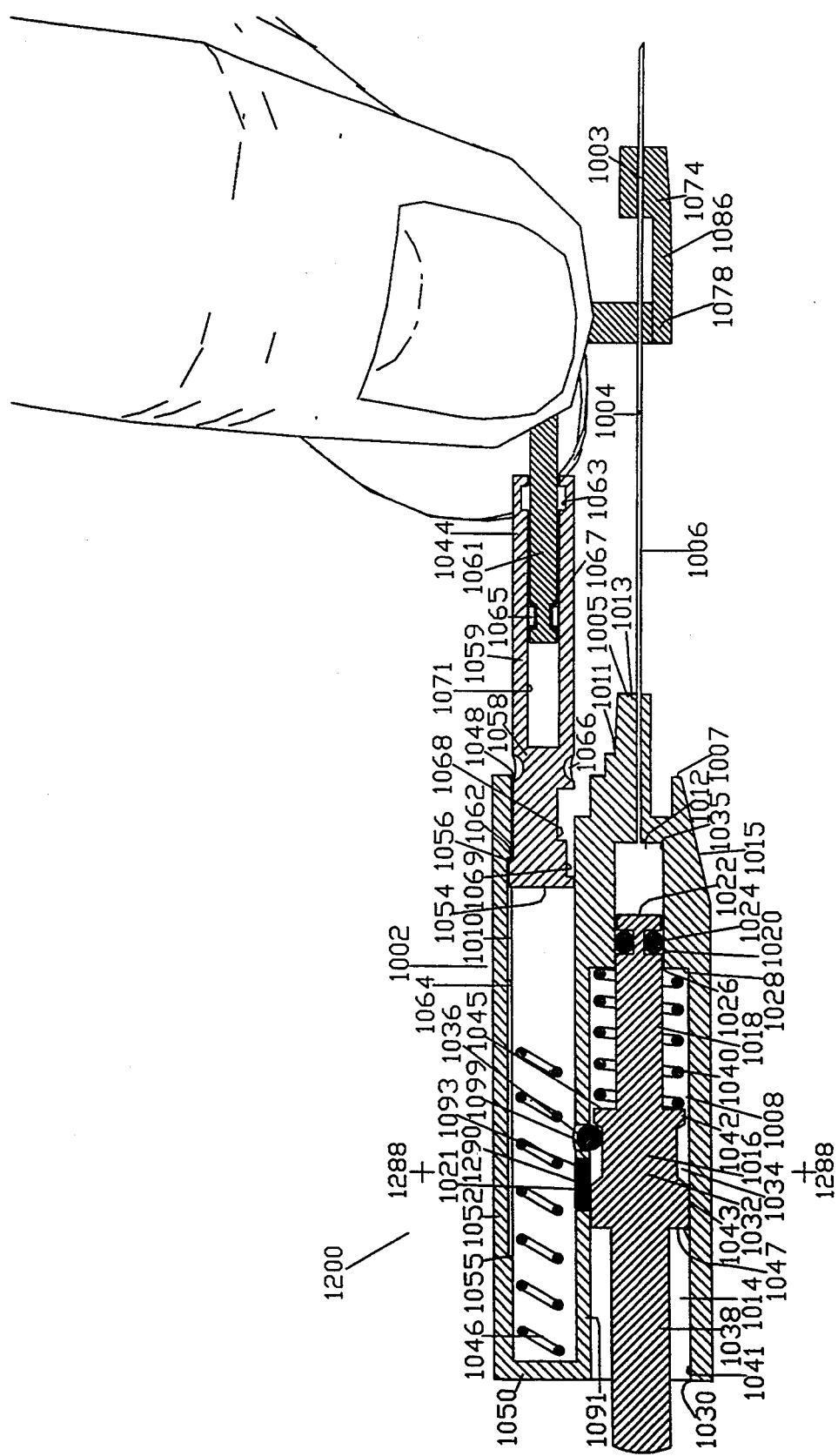
FIG. 30 is a cross section view of another version of the device of FIG. 6 showing needle tip enclosure accomplished via an interface member telescopically arranged.

As shown in FIG. 30, the main body 1058 of the interface member 1044 described in either embodiments represented respectively in FIGS. 1 to 5 and FIGS. 6 to 29, can be also constructed as an extendible member resulting from multiple units 1059 and 1061 partially sliding one over the other, for example as in a telescopic arrangement. Anterior displacement of the distal unit 1061 can be achieved manually or by resilient means and locking between distal unit 1061 and proximal unit 1059 is achieved by irreversible engagement within annular groove 1063 formed in proximal unit 1059 of expandable ring 1065, of round or preferably square cross section, expandable ring which seats in annular groove 1067 of distal unit 1061 and is constrained prior to expansion by rigid wall 1071 of proximal unit 1059.

What is claimed is:

1. A needle stick protector device for an Automatic Cannulation Device, said Automatic Cannulation Device comprising:
    a) a housing,
    b) a hollow needle connected to said housing,
    c) a catheter slideable over said needle,
    d) self-propelling means to automatically advance said catheter to an advanced position into the interior of a blood vessel in response to vanishing of a vacuum created within said housing, said vacuum being created prior to blood vessel penetration, said vanishing of the vacuum occurring upon blood vessel penetration by said needle,
    e) an interface member interposed between said self-propelling means and said catheter, said interface member having a front portion slideable over the needle engaging with said catheter to advance the catheter,
    wherein:

said front portion of said interface member slideable over the needle is also adapted to enclose the tip of said needle upon full forward advancement of said interface member, said forward advancement being self-initiated in response to vanishing of said vacuum occurring upon blood vessel penetration of said needle, and wherein said interface member is irreversibly locked to said housing in its fully advanced position by locking means to provide a needle stick protection with said front portion of said interface member.

2. The device of claim 1 wherein said locking means comprises:

an expanding ring centripetally constrained into an annular recess of said interface member by the presence of walls delimiting a chamber formed in said housing, said chamber slideably receiving said interface member, said expanding ring partially expandable into a corresponding annular groove formed in said walls delimiting said chamber in such a way that, upon full advancement of said interface member, while the outer diameter of said expandable ring engages within said annular groove formed in said walls delimiting said chamber, its inner diameter still engages within said annular recess of said interface member, resulting in an irreversible locking of the interface member to said housing, and, consequently, resulting in an irreversible locking of the front portion of the interface member over the tip of said needle to provide a protection against accidental needle sticks by said needle tip.

3. The device of claim 1 wherein said locking means comprises:

an arrest tooth formed in a wall delimiting a chamber formed in said housing, said chamber slideably receiving said interface member, a correspondent arrest tooth formed in said interface member to engage with arrest tooth formed in said wall of said chamber to provide means for arrest of forward advancement of the interface member, and ball members lodged within recesses formed in said interface member, said recesses being gradually deeper proximally and gradually more shallow distally, said ball members being driven proximally toward said deepening of said recesses upon forward advancement of said interface member, and being driven distally toward said shallowing of said recesses to wedge between said shallowing of recesses and said wall of said chamber to arrest rearward displacement of said interface member upon completed full forward advancement of said interface member, to provide means for rearward arrest of the interface member.

4. The device of claim 1, wherein said interface member advancement to enclose the needle tip is actuated upon backflow of blood occurring upon blood vessel penetration, said blood being drawn by said vacuum pressure within said chamber.

5. The device of claim 1, wherein said advancement of the interface member is a one step operation.

6. The device of claim 1, wherein said advancement of the interface member is a two steps operation.

7. The device of claim 6, wherein said two steps operation comprises a first step advancement of said interface member to a predetermined length, said advancement automatically triggered by said vanishing of vacuum occurring upon blood vessel penetration to automatically advance said catheter into a penetrated blood vessel, and a second step operation wherein the advancement of said interface member is still carried out by said self-propelling means, by manual release of said propelling means initially triggered by said vacuum.

8. The device of claim 5, wherein said two steps operation comprises a first step advancement of said interface member to a predetermined length, said advancement being automatically triggered by said vanishing of vacuum occurring upon blood vessel penetration to automatically advance said catheter into a penetrated blood vessel, and a second step operation wherein the advancement of said interface member is carried out manually, after manual release of said interface member initially triggered by said vacuum.

9. The device of claim 1 wherein said interface member front portion comprises a needle guard of generally hollow cylindrical shape concentric to the needle, said needle guard having an inner diameter comparable to the outer diameter of the needle, said inner diameter of said needle guard being sufficiently greater than the outer diameter of the needle to allow sliding of said guard over said needle up to a forward arrest position, said needle guard being of sufficient length to entirely enclose the needle tip and to extend further anteriorly beyond the needle tip in its forward arrest position.

10. The device of claim 1 wherein said interface member front portion comprises a protective sleeve of generally cylindrical shape concentric to the needle, said protective sleeve having an inner diameter comparable to the outer diameter of the needle, said inner diameter of said protective sleeve being sufficiently greater than the outer diameter of the needle to allow sliding of said protective guard over the needle up to a forward arrest position, said protective sleeve being of sufficient length to entirely enclose the needle tip and to extend further anteriorly beyond the needle tip in its forward arrest position.

11. The device of claim 1 wherein said interface member comprises multiple units sliding one over the other to extend said interface member to a lenght sufficient to enclose the needle tip with said front portion of said interface member when said interface member is fully extended.

* * * * *